(12) United States Patent
Jankauskaite et al.

(10) Patent No.: US 11,033,580 B2
(45) Date of Patent: Jun. 15, 2021

(54) SILICONE MATERIALS HAVING ANTIMICROBIAL EFFICIENCY

(71) Applicant: Kauno Technologijos Universitetas, Kaunas (LT)

(72) Inventors: Virginija Jankauskaite, Kaunas (LT); Aisté Lisauskaite, Kaunas (LT)

(73) Assignee: Kauno Technologijos Universitetas, Kaunas (LT)

( * ) Notice: Subject to any disclaimer, the term of this patent is extended or adjusted under 35 U.S.C. 154(b) by 0 days.

(21) Appl. No.: 16/479,082

(22) PCT Filed: Jan. 17, 2018

(86) PCT No.: PCT/IB2018/050282
§ 371 (c)(1),
(2) Date: Jul. 18, 2019

(87) PCT Pub. No.: WO2018/134742
PCT Pub. Date: Jul. 26, 2018

(65) Prior Publication Data
US 2019/0388466 A1    Dec. 26, 2019

(30) Foreign Application Priority Data
Jan. 20, 2017 (EP) .................... 17152392

(51) Int. Cl.
*A61K 33/38* (2006.01)
*A61K 47/34* (2017.01)
*A61K 47/38* (2006.01)
*A61L 31/00* (2006.01)

(52) U.S. Cl.
CPC .............. *A61K 33/38* (2013.01); *A61K 47/34* (2013.01); *A61K 47/38* (2013.01); *A61L 31/00* (2013.01); *A61L 2300/104* (2013.01); *A61L 2300/404* (2013.01)

(58) Field of Classification Search
CPC ...................................................... A61K 33/38
See application file for complete search history.

(56) References Cited

U.S. PATENT DOCUMENTS

| 9,492,549 B2 | 11/2016 | Löwenhielm et al. |
| 10,111,959 B2 | 10/2018 | Löwenhielm et al. |
| 2006/0159732 A1* | 7/2006 | Cullen .................... A61L 15/64 424/445 |
| 2010/0233245 A1 | 9/2010 | Narayana |
| 2011/0117152 A1 | 5/2011 | Zhu et al. |
| 2013/0101633 A1 | 4/2013 | Löwenhielm et al. |
| 2013/0211308 A1 | 8/2013 | Wan et al. |
| 2015/0189867 A1 | 7/2015 | Kroupa et al. |
| 2017/0080090 A1 | 3/2017 | Lowenhielm et al. |

FOREIGN PATENT DOCUMENTS

RU    2012143888    5/2014

OTHER PUBLICATIONS

International Search Report, PCT/IB2018/050282, dated Apr. 3, 2018.

* cited by examiner

*Primary Examiner* — Benjamin J Packard
(74) *Attorney, Agent, or Firm* — AAA Law

(57) ABSTRACT

Disclosed are antimicrobial silicone substances, which are obtained by using multifunctional cellulose/silver and silicon matrix nanocomposites. Using environmentally friendly, simple deposition techniques, Ag particles were deposited on cellulose. Silicone was filled with the obtained composites of cellulose and silver particles. The created modified cellulose/silver and silicone composite is characterized by good physical and chemical properties, as well as strong antimicrobial effect on both Gram- positive and Gram-negative bacteria.

20 Claims, No Drawings

SILICONE MATERIALS HAVING ANTIMICROBIAL EFFICIENCY

FIELD OF THE INVENTION

The invention relates to antimicrobial silicone materials, which are obtained by using multifunctional cellulose/silver and silicon matrix nanocomposites. Using environmentally friendly, simple deposition techniques, Ag particles were deposited on cellulose. Silicone was filled with the obtained composites of cellulose and silver particles. The created modified cellulose/silver and silicone composite is characterized by good physical and chemical properties, as well as strong antimicrobial effect on both Gram-positive and Gram-negative bacteria.

BACKGROUND OF THE INVENTION

Due to its unique properties, such as thermal and chemical stability, air permeability, elasticity, biocompatibility and bio-durability, silicone is widely used in various fields of health and medicine, for example, in the manufacture of catheters, means for blood transfusion, tubes, contact lenses, hearing valves, breast ergo prostheses, ophthalmological implants, foot inserts and other means and also, in surgery and diagnostic equipment. Silicones, which are used in medicine, must be characterized by antimicrobial effectiveness due to the risk of Our proposed method allows to protect the consumer from problems caused by hospital-acquired infections; these infections (related to health care) form a special group of diseases. The main factors that increase the risk of developing are catheterization of urinary bladder, intravascular catheters, artificial lung ventilation, foreign objects in the body (internal prostheses), burns of a surgical intervention, etc. Also, as much as 80% of infectious diseases spread by contact with hands. While personnel in hospitals and other medical institutions are required to follow strict means for infection control—wash hands and frequently disinfect all surfaces, these measures are clearly insufficient, because the number of contagion in hospitals is growing every year. One of the biggest problems is frequently touched surfaces in intensive care units infested with several hundred to more than 10 000 colonies of infectious bacteria. When treating bacterial infections with antibiotics, most bacteria are killed but some of them are still viable and gain resistance to medicines used. Due to the resistance to antibiotics, it is necessary to use other biocides, which have a strong antimicrobial effect (e.g., silver nanoparticles).

US application US2015189867 describes the methods, in which solid microparticles and silver nanoparticles are dispersed with silicone or silicone is filled with these particles and intended for antimicrobial or other applications. The described method is similar because silver micro- or nanoparticles are used. However, the method presented in our invention is safer because the stable cellulose-silver nanocomposites are created and immobilized in silicone.

The patent application RU2012143888 describes antimicrobial compositions, antimicrobial silicone gel, which is based on said antimicrobial compositions which, among other components, contains a silver salt. The created preparation can be used to treat burns, scars, bacterial infections, viral infections and/or fungal infections. Composites produced by our method described are of solid-phase state and can be used much more widely. Also, by creating stable cellulose/silver nanocomposites a migration of silver nanoparticles having a negative impact on humans is avoided.

There is a known method US2011117152, whereby the silicone characterized by antimicrobial effect contain a silicone rubber, at least one silver containing agent introduced into the silicone rubber, at least one carboxylic acid introduced into the silicone rubber, the surface of which is characterized by antimicrobial activity. The presented method is complicated and requires technologically complex disperse systems. Disperse systems are unstable and lead to increased costs as compared to the case described in the present invention. In our case, simple technology does not require complex technological equipment and the obtained composites are stable.

Our proposed method allows to protect the consumer from problems caused by hospital-acquired infections. There are catheters with silver coating or impregnated with substances characterized by bacterial activity created in the world, but there is a need to create stable composites possessing a very strong antimicrobial effect. The silicone coatings can be used in all areas, which require antimicrobial efficacy.

Such a composition has not been developed and used yet. The silver particles are widely used in the industry, but there is no analogue to multifunctional composites created by us. Successfully developed and evaluated technology of the manufacturing processes has a wide practical application. The composite manufacturing technology developed by us is simple, cheap and fast, it does not require specific composite preparation equipment, the obtained composites are stable and possess a strong antimicrobial effect. The obtained silicone and cellulose/silver composites are biocompatible with human tissues and fluids. All the materials and equipment used are commercially available. There has been a unique dispersion and diffusion system created.

SUMMARY OF THE INVENTION

Aim of the present invention is to create nanocomposites to be used in a silicone matrix as filler, which provides antimicrobial effectiveness and improves the mechanical properties of the material.

Laboratory tests show that the addition of even small amounts of multifunctional filler (5-15%) to silicone significantly improves the mechanical properties of the silicone. Interesting thing is that very small quantities of silver deposited on cellulose and mixed in silicone provides it with a strong antimicrobial effectiveness.

Present invention relates to the silver/cellulose and silicone composite, which comprises (a) silver nanoparticles in an amount of 0.1-7% by weight, preferably 5% by weight, of the total mass of the composite; (b) the oxidized cellulose/silver nanocomposite in an amount of 1-50% by weight, preferably 5-15% by weight, of the total mass of the composite; and (c) silicone.

The forming cellulose described in the present invention is microcrystalline cellulose of a fibrillar form.

The size of particles of microcrystalline cellulose referred to in the present invention is in the range from 20 to 60 µm.

Silicone used to produce the composite of the invention is selected from the group consisting of siloxanes (e.g., polydimethylsiloxane) and silicones (e.g., dimethicone, phenyl dimethicone, phenyl trimethicone, fluorine silicone, amino silicone).

It is important to mention the fact that when the silicone is filled with cellulose/silver nanocomposites tensile strength can be improved by up to 75%.

This invention relates to cellulose/silicone and silver composite, which is in a solid form.

According to one of the embodiments, the silver/cellulose and silicon composite is obtained by preparing silver nanoparticles, cellulose and silicon matrix; by depositing silver nanoparticles on cellulose fiber by exposure of the suspension to microwaves of 450 W for 2 minutes; oxidizing the cellulose/silver composite; introducing the oxidized cellulose/silver nanocomposite in silicone by mixing the components; solidifying the cellulose/silver and silicone composite in order to avoid the migration of silver particles.

According to another embodiment, the cellulose/silver and silicone composite is obtained by preparing silver nano-particles, cellulose and silicon matrix; by depositing silver nanoparticles on the cellulose fiber using cetylmethylammonium bromide solution; by oxidizing the cellulose/silver composite; introducing the oxidized cellulose/silver nanocomposite in the silicone matrix by mixing the components; solidifying the cellulose/silver and silicone composite in order to avoid the migration of silver particles.

The above-described methods for obtaining cellulose/silver and silicone composite use the cellulose, which is microcrystalline cellulose in a fibrillar form.

In the above-described methods for obtaining silver/cellulose and silicon composite silver nano-particles are obtained from a silver salt selected from the group consisting of $AgNO_3$, $Ag_2CO_3$, $Ag_3PO_4$, $Ag_2SO_4$, $Ag_2SO_3$, silver zirconium, organic silver salts, such as silver citrate, silver acetate, silver lactate and combinations or mixtures thereof.

The cellulose/silver and silicone composite solidification step is carried out at temperatures from 30 to 120° C.

Another embodiment of the present invention is that silver nanoparticles are additionally added into the silicone matrix in an amount of 0.1 to 7% by weight, preferably 5% by weight to the total mass of the composite.

The composite obtained using the methods for obtaining the cellulose/silver and silicone composite described in the present invention is intended for the production of antimicrobial substances and used in the manufacture of medical instruments, such as catheters, means for blood transfusion, tubes, contact lenses, hearing valves, breast ergo prostheses, ophthalmological implants, foot inserts, as well as in surgical and diagnostic equipment.

In the embodiments described by the person skilled in the art changes can be created without deviations from the scope of this invention as specified in the following claims.

DETAILED DESCRIPTION OF THE INVENTION

The above description of the preferred embodiments is provided in order to illustrate and describe the present invention. This is not an exhaustive or limiting description, seeking to determine the exact form or embodiment. The above description should be considered more like an illustration, rather than a limitation. It is evident that numerous modifications and variations may be obvious to the persons skilled in the art. Embodiment is chosen and described so that the persons skilled in the art in the best way clarify the principles of this invention and the best practical application for various embodiments with various modifications suitable for a particular use or application of the embodiment. It is intended that the scope of the invention is defined in the claim appended thereto and its equivalents, where all of the said terms have meaning within the widest range, unless indicated otherwise.

The Materials Used and Their Characteristics

Silicone Matrix

A polydimethylsiloxane (PDMS) of a linear structure with terminal vinyl groups was used. This is a two-component A/B silicone, which is solidified by a platinum complex according to the mechanism presented as following:

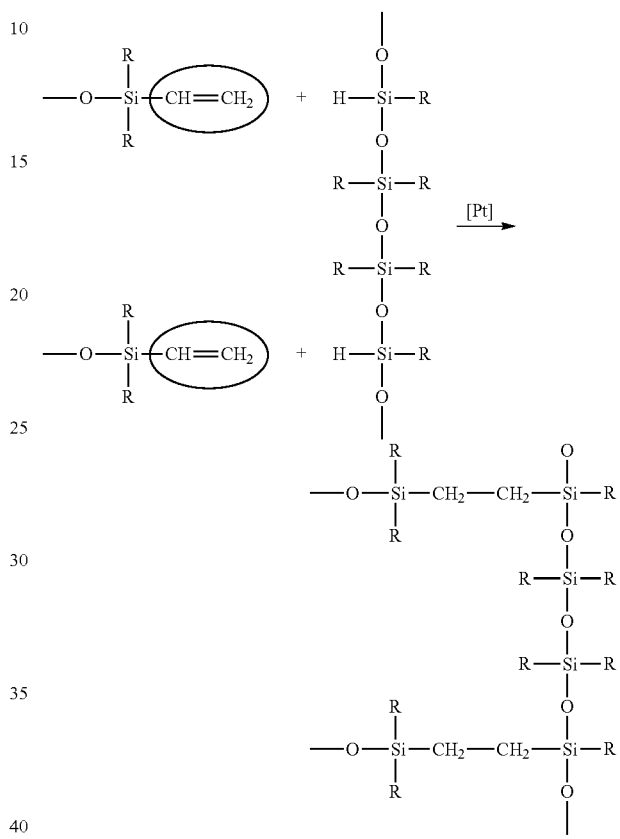

The main characteristics of PDMS used are presented in Table 1.

TABLE 1

| The main characteristics of PDMS | |
|---|---|
| Characteristic | Value |
| Viscosity of mixture A:B = 1:1, Pa · s | 350 (T = 25° C.) |
| Specific density, kg/cm³ | 1.02 (T = 25° C.) |
| Curing duration | 120° C./15 min |
| Durability, h | 16 (T = 25° C.) |
| Thermal conductivity, W/mK | 0.2 |
| Shore hardness A, relative units | 35 |
| Dielectric permittivity, kV/mm | 27 |
| Volumetric resistance, Ωcm | $2.2 \times 10^{14}$ |
| Dielectric constant | 4.5 (T = 25° C., 100 kHz) |
| Dissipation factor | 0.002 (T = 25° C., 100 kHz) |

Microcrystalline Cellulose of Fibrillar Structure

Microcrystalline cellulose (MCC), the main characteristics of which are presented in Table 2, was used as PDMS filler. MCC is obtained when mineral acids partially depolymerize amorphous areas of α-cellulose derived from fibrous plant matter. After hydrolysis of cellulose, predominantly crystalline microfibrils remain.

TABLE 2

Main characteristics of microcrystalline cellulose

| Characteristic | Value |
|---|---|
| Particle size, µm | 18-22 |
| pH | 5-7 (11 wt. %) |
| Density, g/mL | 0.5 (T = 25° C.) |
| Moisture content, % | ≤5.0 |

Silver Nanoparticles

Silver nanoparticles (AgNPs) were synthesized by two different chemical methods. Chemical reagents used for the synthesis of silver nanoparticles are presented in Table 3.

TABLE 3

Chemical reagents used for the synthesis of silver nanoparticles

| Reagent | Chemical formula | Purpose | Manufacturer |
|---|---|---|---|
| Synthesis of AgNPs (1) | | | |
| Silver nitrate | $AgNO_3$ | Precursor | Sigma-Adrich |
| Morpholine | $C_4H_9NO$ | Medium | Sigma-Adrich |
| Oleic acid | $C_{18}H_{34}O_2$ | Stabilizer | Avsista |
| Hydrazine hydrate | $N_2H_4 \cdot H_2O$ | Reducer | Sigma-Adrich |
| Chloroform | $CHCl_3$ | Medium | Sigma-Adrich |
| Distilled water | $H_2O$ | Medium | KTU |
| Synthesis of AgNPs (2) | | | |
| Silver nitrate | $AgNO_3$ | Precursor | Sigma-Adrich |
| Polyvinylpyrrolidone | $(C_6H_9NO)_n$ | Reducer, anticoagulant, stabilizer | Reducer, anticoagulant, stabilizer |
| Distilled water | $H_2O$ | Medium | KTU |

Methods of Synthesis of Silver Nanoparticles

1. Synthesis of Ag NPs (2) by Chemical Reduction in Chloroform Medium

At room temperature, 10 ml of morpholine and 2 g of oleic acid is slowly poured into 20 ml of 0.05 M $AgNO_3$ solution. This solution is stirred and, after it reaches the desired temperature (25-100° C.), 3 ml of hydrazine hydrate is slowly added dropwise. The solution is stirred further until it gets yellow and becomes brown, a lot of foam is formed (it can be counteracted by pouring distilled $H_2O$). Reaction mixture is then stirred for an additional 3 min. at 25-100° C. After cooling, the solution is diluted 1:2 with acetone and centrifuged for 5 minutes 2 times to wash the precipitates. The obtained precipitates are dried in a ventilated electric furnace for ~15 minutes at 20-120° C. Dry powder is dispersed in 50 ml of chloroform. The resulting solution is allowed to settle for 24 hours at room temperature.

2. Synthesis of Ag NPs Colloid by Chemical Reduction in Ethanol Medium

At room temperature, 10 g of polyvinylpyrrolidone (PVP) is dissolved in 80 ml of ethyl alcohol (when the particles are poorly soluble the solution can be heated up to 30-40° C.). Then, 2 g of silver nitrate ($AgNO_3$) dissolved in 10 ml of distilled $H_2O$ is admixed into the resulting solution. The total amount of the mixture is increased to 100 ml by adding alcohol. The resulting solution is allowed to settle for 24 hours at room temperature. $CA_g$=12 mg/ml.

Production of MCC/AgNPs Composite

Before the synthesis of the MCC/AgNPs composites, cellulose was treated with KOH in order to remove lignin.

Treatment of cellulose with KOH or NaOH. 1.2 g of KOH (or NaOH) is dissolved in 200 ml of distilled $H_2O$ and stirred for ~30 min. until the substance is completely dissolved. 10 g of cellulose is added into the obtained solution and stirred for another hour. The resulting cellulose is washed with 2 liters of distilled $H_2O$.

Further treated cellulose and silver particle composites were obtained applying the two chemical synthesis methods. Chemical reagents used for the synthesis of composites are given in Table 4.

TABLE 4

Chemical reagents used for the synthesis of MCC/AgNPs composite

| Reagent | Chemical formula | Purpose | Manufacturer |
|---|---|---|---|
| Synthesis of MCC/AgNPs (1) | | | |
| Cellulose | $(C_6H_{10}O_5)_n$ | Filler | Sigma-Adrich |
| Silver nitrate | $AgNO_3$ | Precursor | Sigma-Adrich |
| Cetyltrimethylammonium bromide | $C_{19}H_{42}BrN$ | Reducer | Sigma-Adrich |
| Sodium borohydride | $NaBH_4$ | Reducer | Sigma-Adrich |
| Distilled water | $H_2O$ | Medium | KTU |
| Synthesis of MCC/AgNPs (2) | | | |
| Cellulose | $(C_6H_{10}O_5)n$ | Filler | Sigma-Adrich |
| Silver nitrate | $AgNO_3$ | Precursor | Sigma-Adrich |
| Ethylene glycol | $C_2H_6O_2$ | Medium | Eurochemicals |

Methods for Synthesis of MCC/AgNPs Composites (1) Synthesis of MCC/AgNPs Composite Three separate solutions are prepared:

Solution A: 0.98 g of cetylmethylammonium bromide (CTAB) is dissolved in 100 ml of distilled $H_2O$.

Solution B: 0.34 g of $AgNO_3$ is dissolved in 50 ml of distilled $H_2O$.

Solution C: 0.16 g of $NaBH_4$ is dissolved in 50 ml of distilled $H_2O$.

A and B solutions were mixed. 10 g of cellulose treated with KOH is poured into the resulting clear homogeneous solution and stirred for 60 minutes. Solution C is slowly dripped into to the suspension and everything stirred for further 2 hours. The resulting cellulose and Ag composite is washed with 1 liter of distilled $H_2O$ and dried in the electric furnace at 20-100±1° C. for 2 hours.

(2) Preparation of MCC/AgNPs Composite 0.34 g of $AgNO_3$ is dissolved in 100 ml of ethylene glycol. Vigorously stirring 2 g of PVP is poured into the solution. 10 g of cellulose is added to the obtained solution and dispersed ultrasonically for 5 minutes. The suspension is placed in a microwave and exposed to 450 W microwaves for 2 minutes.

After the preparation of MCC/AgNPs (1) and MCC/AgNPs (2) composites, they are oxidized in order to increase their antimicrobial effectiveness. Chemical reagents used for oxidation are given in Table 5.

TABLE 5

Chemical reagents used for oxidation of MCC/AgNPs

| Reagent | Chemical formula | Purpose | Manufacturer |
|---|---|---|---|
| Potassium permanganate | $KMnO_4$ | Oxidizer | Valentis |
| Distilled water | $H_2O$ | Medium | KTU |

Oxidation of MCC/AgNPs composite was carried out according to the given methodology. 2 g of $KMnO_4$ was dissolved in 250 ml of distilled $H_2O$. The resulting solution was stirred and heated to 60° C. for 1 hour. Then, the resulting solution is poured into 20 g of CMC/Ag and stirred for another 60 minutes. After cooling, the resulting suspension is rinsed with acetone.

Depending on the MCC/AgNPs composite (1) or (2) is used, the PDMS-MCC/AgNPs composite (1) or (2) was obtained respectively. A stronger antimicrobial activity is obtained introducing also AgNPs. Only by using these two ways of synthesis PDMS becomes fully solid.

(1) Production of PDMS-MCC/AgNPs Composite

The composite is obtained by adding various amounts of oxidized (1) MCC/AgNPs composite (5-30% by weight) to PDMS A:B=1:1. In order to ensure an even distribution of particles of the composite MCC/AgNPs (1) in bi-component PDMS medium, the selected amount of the composite is mixed with 10 ml of chloroform at room temperature and the resulting suspension is dispersed with an ultrasonic probe UP200S with a security box for 30 minutes. Then the homogeneous system is slowly poured into PDMS component A, particles AgNPs (1) (3-7% by weight) are also poured in and the mixture is stirred with a magnetic stirrer at a temperature of 30±10° C. for 2 hours. PDMS component B is added into the obtained homogeneous mixture and continues to mix it intensively for 15 minutes. The resulting composite is poured into the mold and the excess air that got into the mixture during mixing is removed by vacuuming at 0.06 MPa for 60 minutes. Composite-filled molds were placed in a ventilated low-temperature electric furnace SNOL ⁵⁸⁄₃₅₀ (UABMORIS Technology, Lithuania) and heated at 70±20° C. for 30 minutes until PDMS-MCC/AgNPs becomes completely solid (curing).

(2) Preparation of PDMS-MCC/AgNPs Composite

The composite is obtained by adding various amounts of oxidized (2) MCC/AgNPs filler (5-30% by weight) to PDMS A:B=1:1. In order to ensure an even distribution of particles of the composite MCC/AgNPs (2) in bi-component PDMS medium, the selected amount of the filler is mixed with 10 ml of chloroform at room temperature and the resulting suspension is dispersed with an ultrasonic probe UP200S with a security box for 30 minutes. Then the homogeneous system is slowly poured into PDMS component A, particles AgNPs (2) (3-7% by weight) are also poured in and the mixture is stirred with a magnetic stirrer at a temperature of 30±10° C. for 2 hours. PDMS component B is added into the obtained homogeneous mixture and continues to mix it intensively for 15 minutes. The resulting composite is poured into the mold and the excess air that got into the mixture during mixing is removed by vacuuming at 0.06 MPa for 60 minutes. Composite-filled molds were placed in a ventilated low-temperature electric furnace SNOL ⁵⁸⁄₃₅₀ (UAB MORIS Technology, Lithuania) and heated at 70±20° C. for 30 minutes until the silicone becomes completely solid (curing).

The invention claimed is:

1. A composite of a cellulose/silver nanocomposite and a polymer matrix comprising:
    (a) silver nanoparticles in an amount of 0.1 to 7% by weight of the total mass of the composite;
    (b) the cellulose/silver nanocomposite in an amount of 1-50% by weight of the total mass of the composite, wherein the cellulose/silver nanocomposite is oxidized, and wherein the silver nanoparticles are deposited on the cellulose/silver nanocomposite; and
    (c) the polymer matrix, wherein the cellulose/silver nanocomposite is dispersed in the polymer matrix thereby providing a diffusion system,
    wherein the composite has strong and long-lasting antimicrobial activity on both Gram-positive and Gram-negative bacteria, and
    wherein the composite is in solid form.

2. The composite according to claim 1, wherein the cellulose in the cellulose/silver nanocomposite comprises a microcrystalline cellulose of cellulose crystals and cellulose fibers.

3. The composite according to claim 2, wherein the size of particles of microcrystalline cellulose is in the range from 20 to 60 μm.

4. The composite according to claim 1, wherein the polymer matrix is selected from the group consisting of siloxane, polydimethylsiloxane, polyurethane, latex, polyvinyl chloride, rubbers.

5. The composite according to claim 1, wherein the tensile strength of the said composite is improved 75% as compared to the tensile strength of the polymer matrix without the cellulose/silver nanocomposite.

6. A method of production of a composite of a cellulose/silver nanocomposite and a polymer matrix comprising:
    (a) preparing silver nanoparticles, cellulose comprising cellulose fibers, and a silicon matrix;
    (b) depositing the silver nanoparticles on the cellulose fibers by exposing a solution of the silver nanoparticles and the cellulose fibers to microwaves of 450 W for 2 minutes;
    (c) oxidizing the cellulose/silver nanocomposite;
    (d) introducing the oxidized cellulose/silver nanocomposite into the polymer matrix by mixing the components;
    (e) solidifying the mixture of the cellulose/silver nanocomposite and the polymer matrix to form the composite, wherein migration of the silver nanoparticles from the solidified composite is avoided.

7. A method of synthesizing a composite of a cellulose/silver nanocomposite and a polymer matrix comprising:
    (a) preparing silver nanoparticles, cellulose comprising cellulose fibers, and the polymer matrix;
    (b) depositing the silver nanoparticles on the cellulose fiber using a cetylmethylammonium bromide solution to create a cellulose/silver nanocomposite;
    (c) oxidizing the cellulose/silver nanocomposite;
    (d) introducing the oxidized cellulose/silver nanocomposite into the polymer matrix by mixing the components;
    (e) solidifying the mixture of the cellulose/silver nanocomposite and the polymer matrix to form the composite, wherein migration of the silver nanoparticles from the solidified composite is avoided.

8. The method according to claim 7, wherein the cellulose used in step (a) consists of a microcrystalline cellulose of cellulose crystals and the cellulose fibers.

9. The method according to claim 7, wherein in step (a) the silver nanoparticles are obtained from a silver salt selected from the group consisting of $AgNO_3$, $Ag_2CO_3$, $Ag_3PO_4$, $Ag_2SO_4$, $Ag_2SO_3$, silver zirconium, organic silver salts, silver acetate, silver lactate and combinations or mixtures thereof.

10. The method according to claim 7, wherein the solidifying step (e) is carried out at a temperature from 30 to 120° C.

11. The method according to claim 7, wherein the polymer matrix is a silicone matrix and the silver nanoparticles are deposited is an amount such that the silver nanoparticles constitute 0.1-7% by weight of the total mass of the composite.

12. The method according to claim 11, wherein polymer matrix used in step (a) is selected from the group consisting of siloxanes, phenyl dimethicone, phenyl trimethicone, fluorine silicone, amino silicone.

13. A silver/cellulose and matrix composite for the manufacture of antimicrobial substances comprising the composite of claim 1.

14. The composite according to claim 2, wherein the size of particles of microcrystalline cellulose is in the range from 20 to 60 μm.

15. The composite according to claim 2, wherein tensile strength of the said silver/cellulose and matrix composite is up to 75%.

16. The composite according to claim 3, wherein tensile strength of the said silver/cellulose and matrix composite is up to 75%.

17. The method according to claim 12, wherein the cellulose used in step (a) consists of a microcrystalline cellulose of cellulose crystals and the cellulose fibers.

18. The method according to claim 8, wherein in step (a) the silver nanoparticles are obtained from a silver salt selected from the group consisting of $AgNO_3$, $Ag_2CO_3$, $Ag_3PO_4$, $Ag_2SO_4$, $Ag_2SO_3$, silver zirconium, organic silver salts, silver acetate, silver lactate and combinations or mixtures thereof.

19. The method according to claim 8, wherein the solidifying step (e) is carried out at a temperature from 30 to 120° C.

20. The method according to claim 7, wherein the silver nanoparticles are deposited in an amount such that the silver nanoparticles constitute 5% by weight, of the total mass of the composite.

* * * * *